(12) United States Patent
McDonald et al.

(10) Patent No.: US 7,368,546 B2
(45) Date of Patent: May 6, 2008

(54) HUMAN SAA3 NUCLEIC ACID MOLECULE, PROTEIN, AND METHODS OF USE FOR SAME

(75) Inventors: Thomas L. McDonald, Omaha, NE (US); Marilynn A. Larson, Lincoln, NE (US); Annika Weber, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 538 days.

(21) Appl. No.: 10/348,304

(22) Filed: Jan. 21, 2003

(65) Prior Publication Data

US 2004/0142415 A1  Jul. 22, 2004

(51) Int. Cl.
*C07H 21/02* (2006.01)
*C12N 15/00* (2006.01)

(52) U.S. Cl. .................................. 536/23.1; 435/320.1

(58) Field of Classification Search ............... 435/69.1, 435/325, 366; 536/23.1
See application file for complete search history.

(56) References Cited

U.S. PATENT DOCUMENTS

| | | | |
|---|---|---|---|
| 4,377,569 A | 3/1983 | Plymate |
| 4,425,330 A | 1/1984 | Norcross et al. |
| 4,755,380 A | 7/1988 | Grubb |
| 4,952,496 A | 8/1990 | Studier |
| 5,227,301 A | 7/1993 | Turner et al. |
| 5,536,640 A | 7/1996 | Sipe et al. |
| 5,585,098 A | 12/1996 | Coleman |
| 5,700,465 A | 12/1997 | Tao et al. |
| 5,807,684 A | 9/1998 | Simmons et al. |
| 5,853,985 A | 12/1998 | Salbaum |
| 5,952,313 A | 9/1999 | Carlson |
| 5,958,883 A | 9/1999 | Snow |
| 6,004,936 A | 12/1999 | Kisilevsky |
| 6,013,857 A | 1/2000 | Deboer |

FOREIGN PATENT DOCUMENTS

| | | |
|---|---|---|
| EP | 0872 558 A1 | 10/1998 |
| EP | 1 067 194 | 1/2001 |
| WO | WO/95/21625 | 8/1995 |
| WO | WO/97/04317 | 2/1997 |
| WO | WO/97/06184 | 2/1997 |
| WO | WO/98/03206 | 1/1998 |
| WO | WO/98/40506 | 9/1998 |
| WO | WO/99/18227 | 4/1999 |
| WO | WO 01 14580 A1 | 3/2001 |
| WO | WO/01/31006 | 3/2001 |

OTHER PUBLICATIONS

Bowie, et al. Science, 247: 1306-10, 1990.*
Skolnick et al. TIBTECH 18:34-39, 2000.*
Bauman, H., et al., "The acute phase response", IT Review, 1994 Elsevier Science Ltd., 0167-5699/94.
Benson, M. Douglas, "A unique insertion in the primary structure of bovine amyloid AA protein" J. Lab Clin Med., vol. 113:67-72, 1989.
Hirvonen, Juhani, et al, "Acute phase response in heifers with experimentally induced mastitis" Journal of Dairy Research (1996) 63 352-360.
Hulten, C., et al., "The acute phase serum amyloid A protein (SAA) in the horse: isolation and characterization of three isoforms", Veterinary Immmunology and Immunopathology 57(1997) 215-227.
Huszenicza, Gy., et al. "Diagnostic Value of Certain Mastitis Markers in Following up the Clinical and Bacteriological Change in Pharmacotherapeutic Studies" University of Veterinary Science, Budapest, Hungary 45(4) pp. 409-416 (1997).
Jensen, L., et al., "Regulation of serum amyloid A protein expression during the acute-phase response", Biochem J. (1998) 334:489-503.
Kho Y.J., et al., "Cloning and characterization of involution-specific genes from the bovine mammary gland" Database EMBL accession No. AF160867 'Online! Jun. 30, 2000.
Kho, Y.J., et al., GenBank Submission AAF77630, serum amyloid A protein [Bos tauru].
Kho, Y.J., et al., Rapid Communication: Cloning of bovine serum amyloid A3 $_c$DNA$_1$, American Society of Animal Science, May 19, 2000.
Kluve-Beckerman, Barbara et al., "Primary Structures of Dog and Cat Amyloid A Proteins: Comparison to Human AA" Comp. Biochem. Physiol. vol. 94B, No. 1, pp. 175-183, 1989.
Kluve-Beckerman, Barbara, et al. "Human Serum Amyloid A—Three Hepatic mRNAs and the Coresponding Proteins in One Person" The Journal of Clinical Investigation, Inc., vol. 82, Nov. 1988 pp. 1670-1675.
Liang, Jun-shan, et al., "Amino terminao region of acute phase, but not constitutive, serym amyloid A (apoSAA) specifically binds and transports cholesterol into aortic smooth muscle and HepG2 cells", Journal of Lipid Research (1996) 37:2109-2116.
Liepnieks, J., et al., "The primary structure of serum amyloid A protein in the rabbit: Comparison with serum amyloid A proteins in other species", J Lab Clin Med (1991) 118(6):570-576.
Malle, E., "Human serum amyloid A (SAA) protein: a prominent acute-phase reactant for clinical practice", European Journal of Clinical Investigation (1996) 26::427-435.
Marhaug, Gudmund, et al. "Mink Serum Amyloid A Protein. Expression and primary structure based on cDNA", J. Biol. Chem., vol. 265:10049-10054, 1990.
McDonald, T., et al., "A monoclonal antibody sandwich immunoassay for serum amyloid A (SAA) protein", J. of Immunological Methods, 144 (1991) 149-155.

(Continued)

Primary Examiner—Anne Marie Wehbe
Assistant Examiner—Fereydoun G. Sajjadi
(74) Attorney, Agent, or Firm—McKee, Voorhees & Sease, P.L.C.

(57) ABSTRACT

A nucleotide sequence encoding human serum amyloid A3 (SAA3), isolated, purified and characterized from human mammary epithelial cells is disclosed. Proteins encoded thereby and methods of use for the same are also disclosed.

9 Claims, 4 Drawing Sheets

OTHER PUBLICATIONS

McDoanld, T., et al. "Elevated extrahepatic expression and secretion of mammary-associated serum amyloid A3 (M-SAA3) into colostrums" Veterinary Immunology and Immunopathology 6528 (2001) 1-9.

Migita, K., et al., "Serum Amyloid A Protein Induces Production of Matrix Metalloproteinases by Human Synovial Fibroblasts", Laboratory Investigation, 78(5):535-539 (1998).

Mitchell, T., et al., "The acute phase reactant serum amyloid A (SAA3) is a novel substrate for degradation by the metalloproteinases collagenase and stromelysin", Biochem et Biophysica Acta. 1156 (1998) 245-254.

Mitchell, T.I., et al., "Serum Amyloid A (SAA3) Produced by Rabbit Synovial Fibroblasts Treated with Phorbol Esters or Interlaukin 1 induces Synthesis of Collagenase and is Neutralized with Specific Antiserum", *J. Clinical Investigation* 87(4):1177-1185 (1991).

Patel, H., "Human Serium Amyloid A has Cytokine-Like Properties", Scand. J. Immunol. 1998, 48:410-418.

Peristeris, P., "Effects of serum amyloid A protein on lymphocytes, HeLa, and MRC5 cells in culture", Biochem. Cell Biol., (1989) 67:365-370.

Rossevatn, K., et al., "The complete amino acid sequence of bovine serum amyloid protein A (SAA) and of subspecies of the tissue-deposited amyloid fibril protein A", *Scand. J. Immunol.* 35(2):217-24 (1992).

Satoh, Megumi, et al, "Sandwich enzyme-linked immunosorbent assay for quantitative measurement of serum amyloid A protein in horses" Am J Vet Res., vol. 56, No. 10, Oct. 1995.

Sletten, K., "The Primary Structure of Equine Serum Amyloid A (SAA) Protein", *Scand. J. Immunol.* 30(1):117-122 (1989).

Sletten, K., et al., "The Amino Acid Sequence of an Amyloid Fibril Protein AA Isolated from the Horse", Scand. J. Immunol. 26, 79-84, 1987.

Smith, J., et al., "Comparison of Serum Amyloid A and C-Reactive Protein as Indicators of Lung Inflammation in Corticosteroid Treated and Non-Corticosteroid Treated Cystic Fibrosis Patients", Journal of Clinical Laboratory Analysis 6:219-224 (1992).

Smith, J., et al., "Production of serum amyloid A and C-reactive Protein by HepG2 cells stimulated with combinations of cytokines or monocyte conditioned media: the effects of prednisolone", Clin. exp. Immunol. (1992) 783.

Smith, J., et al., "Use of Ethanol-Eluted Hydrophobic Interaction Chromatography in the Purification of Serum Amyloid A", Protein Expression and Purification 2:158-161 (1991).

Steel, D., et al., "Expression and regulation of Constitutive and Acute Phase Serum Amyloid A mRNAs in Hepatic and Non-Hepatic Cell Lines", 1996, Blackwell Science Ltd., Scandinavian Journal of Immunology, 44:493-500.

Steel, D., et al., "The major acute phase reactants: C-reactive protein, serum amyloid P component and serum and amyloid A protein", Review, 1994 Elsevier Science Ltd, 0167-5699/94.

Syversen, P.V., et al., "The Primary Structure of Serum Amyloid A Protein in the Sheep; Comparison with Serum Amyloid A in Other Species" Scand. J. Immuno., vol. 39:88-94, 1994.

Taktak, Y.S., et al., "A solid phase enzyme immunoassay for serum amyloid A (SAA) protein", Journal of Immunological Methods, 136 (1991) 11-16.

Thompson, D., et al., "The value of acute phase protein measurements in clinical practice", Ann Clin Biochem 1992, 29:123-131.

Uhlar, C., "Evolution of the Serum Amyloid A (SAA) Protein Superfamily", Genomics 19:228-235 (1994).

Urieli-Shoval, S., et al., "Widespread Expression of Serum Amyloid A in Histologically Normal Human Tissues: Predominant Localization of the Epithelium", The Journal of Histochemistry & Cytochemistry 46(12):1377-1384 (1998).

Waalen, Kristian, et al., "The Primary Structure of Amyloid Fibril Protein AA in Endotoxin-Induced Amyloidosis of the Mink", European Journal of Biochem, vol. 104:407-412 (1980).

Wilkins, Julie, et al., "Rapid Automated Enzyme Immunoassay of Serum Amyloid A", Clin. Chem. 40/7, 1284-1290 (1994).

Zank, W., et al., "Assessment of Subacute Mammary Inflammation by Soluble Biomarkers in Comparison to Somatic Cell Counts in Quarter Milk Samples from Dairy Cows", J. Vet. Med. A45, 41-51 (1998).

Zimlichman, S., "Serum amyloid A, an acute phase protein, inhibits platelet activation", Serum amyloid A and platelet activation, 116(2):180-186.

Database CAPLUS on STN, AN 1993: 11776, Kluve-Beckerman, B. et al. "Sequence Analysis of a Third Human SAA gene"., Amyloid Amyloidosis Int. Symp. Amyloidosis, 1991. Meeting abstract.

Sellar, et al. Organization of the Region Encompassing the Human Serum Amyloid A (SAA) Gene Family on Chromosome 11p15.1. Genomics. 1994, vol. 23, pp. 492-495.

Larson et al., "Human serum amyloid A3 peptide enhances intestinal MUC3 expression and inhibits EPEC adherence", pp. 531-540, Biochemical and Biophysical Research Communications 300, Elsevier Science, 2002.

Larson et al., "Induction of human mammary-associated serum amyloid A3 expression by prolactin or lipopolysaccharide", pp. 1030-1037, Biochemical and Biophysical Research Communications 301, Elsevier Science, 2003.

Newstead, D.F., Acceptable levels of bovine immunoglobulin in colostrums testing:, New Zealand Journal of Dairy science and Technology, vol. 6, No. 2, p. 2, Xp008036075, 1971.

Nielsen et al., "Acute phase protein concentrations in serum and milk from healthy cows, cows with clinical mastitis and cows with extramammary inflammatory conditions", The Veterinary Record, vol. 154, No. 12, pp. 361-365, ISSN: 0042-4900, Mar. 20, 2004.

Rygg et al., "In vitro evaluation of an enhanced Human Serum Amyloid A (SAA) Promoter-regulated soluble TNF Receptor Fusion Protein for Anti-inflammatory Gene Therapy", Scand J Immunol, 2001.

Schrodl et al., "C-reaction protein as a new parameter of mastitis's!", Tierarztlich Praxis, vol. 23, No. 4, pp. 337-341, XP008036085, ISSN: 0303-6286, 1995.

Sipe et al., "Direct binding enzyme-linked immunosorbent assay (Elisa) for serum amyloid A (SAA)", Journal of Immunological Methods, Elsevier Science, Publishers B.V. Amsterdam, NL, vol. 125, No. 1/2, pp. 125-135, XP002018648, ISSN: 0022-1759, 1989.

Kluve-Beckerman, "Nonexpression of the Human Serum Amyloid A Three (SAA3) Gene", DNA and Cell Biology, 10(9):651-661 (1991).

McDonald, "A monoclonal antibody sandwich immunoassay for serum amyloid A (SAA) protein", J. of Immunolog. Methods, 144:149-155 (1991).

McDonald, "Elevated extrahepatic expression and secretion of mammary-associated serum amyloid A3 (M-SAA3) into colostrum", Veterinary Immunology & Immunopathology 6528:1-9 (2001).

Pedersen, "The biology of eukaryotic promoter prediction-a review", Computers & Chemistry 23:191-207 (1999).

Sack, "The human serum amyloid A (SAA)-encoding gene GSAA1:nucleotide sequence and possible autocrine-collagenase-inducer function", Gene, 84:509-515 (1989).

Sletten, "The Primary Structure of Equine Serum Amyloid A (SAA) Protein", Scand. J. Immunol. 30:117-122 (1989).

Zimlichman, S., "Serum amyloid A, an acute phase protein, inhibits platelet activation", Serum amyloid A and platelet activation, 116(2):180-186, (1990).

Kho Y.J., et al., "Cloning and characterization of involution-specific genes from the bovine mammary gland" DATABASE EMBL accession No. AF160867 'Online! Jun. 30, 2000.

\* cited by examiner

Fig. 2

```
M-SAA3   AACTTGAAACAGAATGTGTATTATCCTTGGTTGTGTTTCCTTGGCCCTGC         50
             || |           |   || ||   |     ||
X13895                        ATAGTGGAGATGGGGTCTTGCTATGTTTCCC    31

F1 primer       →
M-SAA3   AGCAGGATGAAGCTCTCCTCTGGCATCATTTTCTGCTCCCTGGTCCTGGG        100
         ||||||||||||||||||||| ||||||||||||||||||||||||||||
X13895   AGCAGGATGAAGCTCTCCACTGGCATCATTTTCTGCTCCCTGGTCCTGGG         81
                                                        intron 1
                                                           ↓
M-SAA3   TGTCAGCAGCCAAGGATGGTTAACATTCCTCAAGGCAGCTGGCCAAGGGA        150
         |||||||||||||||||||||||||||||||||||||||||||||||||
X13895   TGTCAGCAGCCAAGGATGGTTAACATTCCTCAAGGCAGCTGGCCAAGGGG        131

←     R1 primer
M-SAA3   CTAAAGACATGTGGAAAGCCTACTCTGACATGAAAGAAGCCAATTACAAA        200
         |  ||||||||||| |||||||||||||||||||||||||||||||||||
X13895   CAAAAGACATGTGGAGAGCCTACTCTGACATGAAAGAAGCCAATTACAAA        181

*
M-SAA3   AAATTCAGACAAATACTTCCATGCTTGGGGGAACTATGATGCTGTACAAA        250
         ||| |||||||||||||||||||| ||||||||||||||||||||||||
X13895   AAA-TCAGACAAATACTTCCATGCTCGGGGGAACTATGATGCTGTACAAA        230

M-SAA3   GGGGGCTTGGGGCTGTCTGGGCTACAGAAGTGATCAGGTAATGCACATTC        300
         |||| | |||||  ||||||||||||||||||||||
X13895   GGGGCCCTGGGGGTGTCTGGGCTACAGAAGTGATCAG-------------        265

M-SAA3   CTGATGTTGCCAGGAATGAGTGAGCAGAGCTTGACTGCCTTGGACAGTCA        350

X13895   --------------------------------------------------        265
                      intron 2
                         ↓
M-SAA3   GGAGAGAGCGATGCCAGAGAGAACGTCCAGAGACTCACAGGAGACCATGC        400
                 |||||||||||||||||||||||||||||||||||||||||||
X13895   -------CGATGCCAGAGAGAACGTCCAGAGACTCACAGGAGACCATGC         309

M-SAA3   AGAGGATTCGCTGGCTGGCCAGGCTACCAACAAATGGGGCCAGAGTGGCA        450
         ||||||||||||||||||||||||||||||||||||||||||||||||||
X13895   AGAGGATTCGCTGGCTGGCCAGGCTACCAACAAATGGGGCCAGAGTGGCA         359
```

Fig 2. (cont.)

```
M-SAA3   AAGACCCCAATCACTTCCGACCTGCTGGCCTGCCAGAGAAATACTGAGCT    500
         ||||||||||||||||||||||||||||||||||||||||||||||||||
X13895   AAGACCCCAATCACTTCCGACCTGCTGGCCTGCCAGAGAAATACTGAGCT    409

M-SAA3   TCCTTTTCAATCTGCTCTCAGGAGACCTGGCTGTGAGCCCCTGAGGGCAG    550
         | ||||||||||||||| ||||||||| |||||||  |||||||||||||
X13895   T-CTTTTCAATCTGCTCTGAGGAGACCT-GCTGTGA--CCCTGAGGGCAG    455

M-SAA3   GGACATTTGTTGACCTACAGTTAC-TGAATTCTATATCCCTAGTACTTGA    599
         |||||||||||||||||||||||| |||||||||||||||||||||||||
X13895   GGACATTTGTTGACCTACAGTTACTTGAATTCTATATCCCTAGTACTTGA    505 poly(A) signal
M-SAA3   TATAGAACACATAAAAATGCTTAATAAATGCTTGTGAAATCCAAAAAAAA    649
         ||||||||||||||||||||||||||||||||||||||||||||
X13895   TATAGAACACATAAAAATGCTTAATAAATGCTTGTGAAATCCA          548

M-SAA3   AAAAAA                                                655
```

Fig. 3

```
mou-SAA3   MKPSIAIILCILILGVDSQRWVQFMKEAGQGSRDMWRAYSDMKKA   45
ham-SAA3   MKPFLAIIFCFLILGVDSQRWFQFMKEAGQGSTDMWRAYSDMREA   45
rab-SAA3   MKLSIGIIFCFLILGVNSREWLTFLKEAGQGAKDMWRAYSDMKEA   45
bov-SAA3   MNLSTGIIFCFLILGVSSQRWGTFLKEAGQGAKDMWRAYQDMKEA   45
hum-SAA3   MKLSSGIIFCSLVLGVSSQGWLTFLKAAGQGTKDMWKAYSDMKEA   45 mou-SAA3   NWKNSDKYFHARGNYDAARRGPGGAWAAKVISDAREAVQKFTG--   88
ham-SAA3   NWKNSDKYFHARGNYDAAKRGPGGAWAAKVISDAREGIQRFTG--   88
rab-SAA3   NYKNSDKYFHARGNYDAAKRGPGGVWAAEVISDARENYQKLIG--   88
bov-SAA3   NYRGADKYFHARGNYDAARRGPGGAWAAKVISNARETIQGITDPL  90
hum-SAA3   NYKKFRQILPCLGEL                               60 mou-SAA3   -HG------AEDSRADQFANEWGRSGKDPNHFRPAGLPKRY    122
ham-SAA3   -RG------AADSRADQFANKWGRSGKDPNHFRPAGLPSKY    122
rab-SAA3   -RG------AEDSKADQEANQWGRSGNDPNHFRPKGLPDKY    122
bov-SAA3   FKGMTRDQVREDSKADQFANEWGRSGKDPNHFRPAGLPDKY    131
```

HUMAN SAA3 NUCLEIC ACID MOLECULE, PROTEIN, AND METHODS OF USE FOR SAME

FIELD OF THE INVENTION

The present invention relates to the field of immunology and mammalian immune systems. In particular, the invention provides a novel cDNA and isoform of serum amyloid A, SAA3, which had heretofore been considered nonexistent as its gene was characterized as a pseudogene.

BACKGROUND OF THE INVENTION

Several scientific or patent publications are referenced in this patent application to describe the state of the art to which the invention pertains. Each of these publications is incorporated by reference herein, in its entirety.

Mammals respond to tissue injury, trauma or infection by executing a complex series of biological reactions in an effort to prevent further tissue damage, to initiate repair of damaged tissue, and to isolate and destroy infective organisms. This process is referred to as the inflammatory response, the early and intermediate stages of which are referred to as the acute phase response.

The acute phase response involves a wide variety of mediators, including cytokines, interleukins and tumor necrosis factor. It also involves a radical alteration in the biosynthetic profile of the liver. Under normal circumstances, the liver synthesizes a range of plasma proteins at steady state concentrations. Some of these proteins, the "acute phase" proteins are induced in the inflammatory response to a level many times greater than levels found under normal conditions. Acute phase proteins are reviewed by Steel & Whitehead (Immunology Today 15: 81-87, 1994).

One of the massively induced acute phase proteins is serum amyloid A (SAA). SAAs are small apolipoproteins that accumulate and associate rapidly with high-density lipoprotein 3 ($HDL_3$) during the acute phase of the inflammatory response. Most SAA isoforms are induced in response to inflammation; however, certain SAAs (e.g., human SAA4) appear to be constitutively expressed or minimally induced in the inflammatory response.

Serum amyloid A proteins (SAA) comprise a superfamily of apolipoproteins produced in all vertebrates investigated to date (C. M. Uhlar, A. S. Whitehead, Serum amyloid A, the major vertebrate acute-phase reactant, Eur. J. Biochem. 265 (1999) 501-523). Depending on the species, three or four genetic loci that encode SAA have been identified and these genes are differentially expressed hepatically and/or extrahepatically (J. D. Sipe, Serum amyloid A: from fibril to function. Current status, Amyloid: Int. J. Exp. Clin. Invest. 7 (2000) 10-12). Acute phase serum amyloid A proteins (A-SAA) are predominately synthesized by the liver and are largely associated with the high-density lipoprotein 3 ($HDL_3$) fraction of plasma (G. A. Coetzee, A. F. Strachan, D. R. Van Der Westhuyzen, H. C. Hoffe, M. S. Jeenah, F. C. De Beer, Serum amyloid A-containing human high density lipoprotein, J. Biol. Chem. 261 (1986) 9644-9651; N. Eriksen, E. P. Benditt, Isolation and characterization of the amyloid-related apoprotein (SAA) from human high density lipoprotein, Proc. Natl. Acad. Sci. USA 77 (1980) 6860-6864). Hepatically derived A-SAA levels can increase 1000-fold during the acute phase in response to the inflammatory cytokines IL-1, IL-6, and TNF-α (L. E. Jensen, A. S. Whitehead, Regulation of serum amyloid A protein expression during the acute-phase response, Biochem. J. 334 (1998) 489-503). The dramatic increase of A-SAA in circulation is achieved mainly by increased transcription (C. M. Uhlar, A. S. Whitehead, Serum amyloid A, the major vertebrate acute-phase reactant, Eur. J. Biochem. 265 (1999) 501-523).

The liver has been considered the primary site of SAA production. However, SAA production outside the liver has been found, on a limited basis. For instance, expression of SAA mRNA has been reported in human atherosclerotic lesions and in human cultured smooth muscle cells and monocyte/macrophage cell lines (Meek et al., 1994; Urieli-Shoval et al., 1994; Yamada et al., 1996), and a unique isoform of SAA (SAA3) is produced by rabbit synovial fibroblasts (Mitchell et al., J. Clin. Invest. 87: 1177-1185, 1991). More recently, it was discovered that SAA mRNA is widely expressed in many histologically normal epithelial tissues, including tissues of stomach, intestine, tonsil, breast, prostate, thyroid, lung, pancreas, kidney, skin and brain neurons (Urieli-Shoval et al., J. Histochem. Cytochem. 46: 1377-1384, 1998).

Experimental evidence from numerous investigators suggests a variety of functions for SAA proteins including suppression of immune responses (M. A. Aldo-Benson, M. D. Benson, SAA suppression of immune response in vitro: evidence for an effect on T cell-macrophage interaction, J. Immunol. 128 (1982) 2390-2392); inhibition of platelet aggregation (S. Zimlichman, A. Danaon, I. Nathan, G. Mozes, R. Shainkin-Kestenbaum, Serum amyloid A, an acute phase protein, inhibits platelet activation, J. Lab. Clin. Med. 116 (1990) 180-186); involvement in cholesterol/lipid metabolism (R. Kisilevsky, L. Subrahmanyan, Serum amyloid A changes high density lipoprotein's cellular affinity. A clue to serum amyloid A's principal function, Lab. Invest. 66 (1992) 778-785; R. L. Meek, N. Eriksen, E. P. Benditt, Murine serum amyloid A3 is a high density apolipoprotein and is secreted by macrophages, Proc. Natl. Acad. Sci. USA 89 (1992) 7949-7952); participation in detoxification of endotoxin (C. Baumberger, R. J. Ulevitch, J. M. Dayer, Modulation of endotoxic activity of lipopolysaccharide by high-density lipoprotein, Pathobiology 59 (1991) 378-383); induction of collagenase activity (C. E. Brinckerhoff, T. I. Mitchell, M. J. Karmilowicz, B. Kluve-Beckerman, M. D. Benson, Autocrine induction of collagenase by serum amyloid A-like and $_2$-microglobulin-like proteins, Science 243 (1989) 655-657); inhibition of neutrophil oxidative burst (R. P. Linke, V. Bock, G. Valet, G. To the, Inhibition of the oxidative burst response of N-formyl peptide-stimulated neutrophils by serum amyloid A protein, Biochem. Biophys. Res. Commun. 176 (1991) 1100-1105; M. E. Gatt, S. Urieli-Shoval, L. Preciado-Patt, M. Fridkin, S. Calco, Y. Azar, Y. Matzner, Effect of serum amyloid A on selected in vitro functions of isolated human neutrophils, J. Lab. Clin. Med. 132 (1998) 414-420); induction of migration of monocytes, polymorphonuclear leukocytes and T cells (R. Badaloto, J. M. Wang, W. J. Murphy, A. R. Lloyd, D. F. Michiel, L. L. Bausserman, D. J. Kelvin, J. J. Oppenheim, Serum amyloid A is a chemoattractant: induction of migration, adhesion and tissue infiltration of monocytes and polymorphonuclear leukocytes, J. Exp. Med. 180 (1994) 203-209; L. Xu, R. Badolato, W. J. Murphy, D. L. Longo, M. Anver, S. Hale, J. J. Oppenheim, J. M. Wang, A novel biologic function of serum amyloid A. Induction of T lymphocyte migration and adhesion, J. Immunol. 155 (1995) 1184-1190); and inhibition of cell adhesion to extracellular matrix components (L. Preciado-Patt, D. Levartowsky, M. Pras, R. Hershkoviz, O. Likder, M. Fridkin, Inhibition of cell adhesion to glycoproteins of the extracellular matrix by peptides corresponding to serum amyloid A. Toward understanding the physiological role of an enigmatic protein, Eur. J. Biochem. 223 (1994) 35-42). However, the primary physiological role of SAA in normal and disease states is not well understood.

Extrahepatic expression of human SAA mRNA and proteins has been demonstrated in macrophage, adipose, smooth muscle, and endothelial cells, suggesting a probable function at the site of production. Urieli-Shoval et al. determined that extrahepatic expression of human SAA was localized predominately to the epithelial components of a variety of tissues (S. Urieli-Shoval, P. Cohen, S. Eisenberg, Y. Matzner, Widespread expression of serum amyloid A in histologically normal human tissues: predominant localization to the epithelium, J. Histochem. Cytochem. 46 (1998) 1377-1384).

In humans there are four SAA genes clustered on chromosome 11p15.1 (G. C. Sellar, S. A. Jordan, W. A. Bickmore, J. A. Fantes, V. van Heyningen, A. S. Whitehead, The human serum amyloid A protein (SAA) superfamily gene cluster: mapping to chromosome 11p15.1 by physical and genetic linkage analysis, Genomics 19 (1994) 221-227). The hyperinducible SAA1 and SAA2 genes encode 104 residue A-SAA proteins that are 90% identical. SAA1 and SAA2 share approximately 95% overall nucleotide sequence identity in their promoter regions, exons, and introns (J. C. Betts, M. R. Edbrooke, R. V. Thakker, P. Woo, The human acute-phase serum amyloid A gene family: structure, evolution and expression in hepatoma cells, Scand. J. Immunol. 34 (1991) 471-482; P. Woo, J. Sipe, C. A. Dinarello, H. R. Colten, Structure of a human serum amyloid A gene and modulation of its expression in transfected L cells, J. Biol. Chem. 262 (1987) 15790-15795). Despite their sequence similarity, a recent study has demonstrated the differential glucocorticoid enhancement of SAA1 transcriptional expression compared to SAA2 in the context of cytokine-dependent induced expression (C. F. Thorn, A. S. Whitehead, Differential glucocorticoid enhancement of the cytokine-driven transcriptional activation of human acute phase serum amyloid A genes, SAA1 and SAA2, J. Immunol. 169 (2002) 399-406). Human SAA4, initially described by Betts et al. (J. C. Betts, M. R. Edbrooke, R. V. Thakker, P. Woo, The human acute-phase serum amyloid A gene family: structure, evolution and expression in hepatoma cells, Scand. J. Immunol. 34 (1991) 471-482), encodes constitutive SAA4 (C-SAA4) (D. M. Steel, G. C. Sellar, C. M. Uhlar, S. Simon, F. C. DeBeer, A. S. Whitehead, A constitutively expressed serum amyloid A protein gene (SAA4) is closely linked to, and share structural similarities with, an acute-phase serum amyloid A protein gene (SAA2), Genomics 16 (1993) 447-454; A. S. Whitehead, M. C. de Beer, D. M. Steel, M. Rits, J. M. Lelias, W. S. Lane, F. C. de Beer, Identification of novel members of the serum amyloid A protein superfamily as constitutive apolipoproteins of high density lipoproteins, J. Biol. Chem. 267 (1992) 3862-3867). In contrast to A-SAA1 and A-SAA2, C-SAA4 is not significantly induced during an acute phase response. C-SAA4 is 8 residues longer than A-SAA1 and A-SAA2 and shares only 55% identity with either A-SAA protein. C-SAA4 is present at low levels on both normal and acute phase $HDL_3$, suggesting a probable housekeeping function for this protein.

The human SAA3 gene was initially identified by Sack and Talbot and was predicted to encode a 104 residue protein with 71% identity to A-SAA (G. H. Sack, C. C. Talbot, Jr., The human serum amyloid A (SAA)-encoding gene GSAA1: nucleotide sequence and possible autocrine-collagenase-inducer function, Gene 84 (1989) 509-515). However, a later genome-based study determined that a single nucleotide insertion within the predicted exon 3 would result in a truncated human SAA3 protein (B. Kluve-Beckerman, M. L. Drumm, M. D. Benson, Nonexpression of the human serum amyloid A three (SAA3) gene, DNA Cell Biol. 10 (1991) 651-661). To date, the SAA3 transcript or protein has not been detected in the human tissues or cell lines examined, nor has the region presumed to be the promoter of SAA3 been shown to be active (S. Urieli-Shoval, P. Cohen, S. Eisenberg, Y. Matzner, Widespread expression of serum amyloid A in histologically normal human tissues: predominant localization to the epithelium, J. Histochem. Cytochem. 46 (1998) 1377-1384); B. Kluve-Beckerman, M. L. Drumm, M. D. Benson, Nonexpression of the human serum amyloid A three (SAA3) gene, DNA Cell Biol. 10 (1991) 651-661; S. Urieli-Shoval, R. L. Meek, R. H. Hanson, N. Eriksen, E. P. Benditt, Human serum amyloid A genes are expressed in monocyte/macrophage cell lines, Am. J. Pathol. 145 (1994) 650-660; G. C. Sellar, A. S. Whitehead, Localization of four human serum amyloid A (SAA) protein superfamily genes to Chromosome 11p: Characterization of a fifth SAA-related gene sequence, Genomics 16 (1993) 774-776). These studies suggested that the SAA3 gene was either a pseudogene or the appropriate inducing conditions and/or cell type for SAA3 expression were not used.

Applicants have for the first time identified and demonstrated induced expression of the SAA3 gene and identified the transcript (cDNA) in human cells. It is an object of the present invention to provide the human SAA3 transcript and protein encoded thereby.

It is yet another object of the invention to provide nucleotide sequences which encode the human SAA3 protein.

It is yet another object of the invention to provide the amino acid sequence which comprises the human SAA3 protein.

It is yet another object of the invention to provide recombinant DNA protocols for using the sequences of the invention for production of recombinant SAA3, for use in assays to further delineate the role of SAA3 expression, for further understanding the acute phase immune response etc.

It is yet another object of the invention to provide assays for identifying inducers of SAA3 expression such as lipopolysaccharide (LPS) or prolactin (PRL) and to provide a promoter region capable of inducing expression in a human cell of operably linked sequences in the presence of these compounds.

SUMMARY OF THE INVENTION

According to the invention, a human serum amyloid A3 (SAA3) protein is provided, which has been isolated and purified from human mammary epithelial cells.

According to another aspect of the invention, an isolated nucleic acid molecule that encodes a mammalian human SAA3 is provided. The nucleic acid molecule may be a gene, cDNA or RNA and may be single-stranded or double stranded. In a preferred embodiment, the nucleic acid molecule comprises a sequence that encodes SEQ ID NO: 2, or its conservatively modified variants. In a most preferred embodiment the nucleic acid molecule comprises (SEQ ID NO:1) or its conservatively modified variants, including other expressed human SAA3 sequences, a similarly identified sequence, or any other nucleic acid sequence which encodes a LPS or prolactin induced SAA sequence as described in the teachings herein.

According to the invention the sequence for human SAA3 has been determined including the intron regions and the flanking region. Thus the invention also includes a nucleotide sequence which encodes expressed human SAA3 which includes one or more of the native noncoding or intron regions or their conservatively modified variants.

According to another aspect of the invention, antibodies immunologically specific for one or more epitopes of human SAA3 are provided. Preferably, the antibodies are immunologically specific for at least one epitope of the human SAA3 that distinguishes human SAA3 from serum SAA.

In yet another embodiment, the promoter region natively associated with human SAA3 can be used for transgenic protocols or to stimulate SAA production to aid in treatment of diseases associated with the teats or other mammary tissue of animals. For example, the human SAA3 promoter is induced by prolactin. Thus one could administer prolactin or other human SAA3 inducing agent to stimulate its production and cause increased SAA3 by the mammary tissue of said animal. The promoter region also provides mammary tissue specificity for expression of heterologous nucleotide sequences in mammary cells.

In human as well as bovine, mammary associated SAA3 has an ability to stimulate mucin 3 (MUC3) production. Thus the SAA3 may be used to treat and prevent enteric infections or other disease states associated with insufficient levels of mucin, such as traveler's diarrhea, infant diarrhea, necrotizing enterocolitis, urinary tract infections, and provide veterinary medicine a means for preventing diarrhea in herd animals. The invention thus includes pharmaceutical compositions comprising a pharmaceutically effective amount of SAA3 peptide and a carrier to treat these and other diseases with similar pathology. Finally, other epithelial cell linings of mucosal surfaces such as nasopharynx, bladder etc., which produce mucins may also be treated with the pharmaceutical compositions of the invention to stimulate mucin production to prevent or treat infections associated therewith.

In yet another embodiment the invention comprises an assay for studying the effects of SAA expression in mammary and other cells and to further elucidate the role of SAA in inflammation or tissue injury. The sequences herein may also be used to identify other SAA isoforms or to diagnose mastitis or other mammary tissue diseases or injuries associated with inflammation or infection of mammary tissue.

Other features and advantages of the present invention will be better understood by reference to the drawings, detailed descriptions and examples that follow.

BRIEF DESCRIPTION OF THE DRAWINGS

FIG. 2 is a comparison of the human M-SAA3 cDNA sequence described in this application with the originally predicted cDNA sequence for the human SAA3 gene (GenBank accession no. X13895) (SEQ ID NOS:3 and 4). The BESTFIT program in the GCG package (version 10.2) was used to obtain the nucleotide sequence alignment. Identical nucleotides are indicated with a vertical line and dashes represent gaps introduced to maximize similarity. The number of nucleotides from the 5' end of the human SAA3 cDNA sequence is denoted to the right. The location of the human SAA3-specific forward F1 and reverse R1 primers used to generate the initial 123 bp RT-PCR product is identified above the appropriate nucleotide sequence and the orientation of each primer is indicated by an arrow. The predicted translational start codon is in bold type and underlined. The splice site junction for intron 1 and intron 2 in the M-SAA3 transcript are denoted above the junctions with a downward arrow. An asterisk denotes the single base insertion that results in a frameshift for the deduced M-SAA3 protein. Bold type and a double underline designates the predicted translational stop codon. The poly(A) signal is indicated above the underlined consensus sequence for polyadenylation and the poly(A) tail is in bold type.

FIG. 3 is a comparison of the predicted human SAA3 protein with the SAA3 isoform from rabbit, hamster, bovine, and mouse. The amino acid sequence alignment was obtained using the PILEUP program in the GCG package. The accession number is denoted below following the corresponding abbreviation for the mammal and SAA3 protein: rab-SAA3=rabbit SAA3 (GenBank M64696) (SEQ ID NO: 17), ham-SAA3=hamster SAA3 (GenBank M33431) (SEQ ID NO:18), bov-SAA3=bovine SAA3 (GenBank AF335552) (SEQ ID NO:19), mou-SAA3=mouse SAA3 (SWISS-PROT P04918) (SEQ ID NO: 20), and hum-SAA3=human SAA3 (SEQ ID NO:21). Identical or similar residues in at least three SAA3 isoforms are highlighted by a dark background and dashes represent gaps introduced to maximize similarities. The number of residues from the N-terminus of the precursor protein is denoted to the right after the appropriate SAA3 isoform and the presumed cleavage site of the signal peptide is indicated by an inverted triangle (∇).

DETAILED DESCRIPTION OF THE INVENTION

I. Definitions

Figure 1:
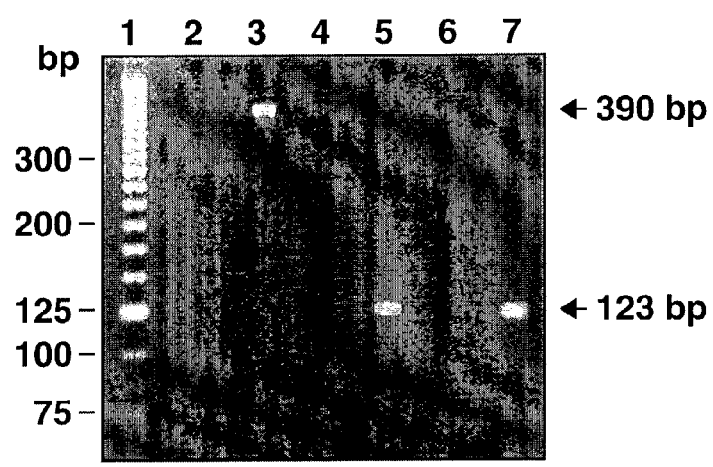
FIG. 1 is a gel showing RT-PCR analysis of M-SAA3 mRNA isolated from the human mammary gland epithelial cell line MCF-7 prior to and after stimulation with either lipopolysaccharide (LPS) or prolactin (PRL). The human SAA3-specific F1 and R1 primers (Table 1) used in RT-PCR correspond to the nucleotides that code for residues in the predicted exons 2 and 3 (GenBank accession no. X13895) or exons 1 and 2 determined in this study. Lane 1, DNA marker; 2, a representative RT-PCR amplification of a cDNA sample prepared without reverse transcriptase; 3, a representative RT-PCR amplification of a cDNA sample prepared from unstimulated mammary gland epithelial cells using human GAPDH-specific primers; 4, unstimulated MCF-7 cells; 5, PRL stimulated MCF-7 cells; 6, unstimulated MCF-7 cells; 7, LPS stimulated MCF-7 cells.

Various terms relating to the compositions and methods of the present invention are used herein above and also throughout the specification and claims.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, the terms "SAA3" and "M-SAA3" are used interchangeably and include but are not limited to the sequences disclosed herein, their conservatively modified variants, regardless of source and any other variants which retain the biological properties of the SAA3 and as demonstrated by the assays disclosed and incorporated herein.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences and is intended to be included whenever a reference to a specific sequence is made. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium Mycoplasma capricolum, or the ciliate Macronucleus, may be used when the nucleic acid is expressed therein.

When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

With respect to proteins or peptides, the term "isolated protein (or peptide)" or "isolated and purified protein (or peptide)" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below). As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as $E.$ $coli$, or eukaryotic cells such as yeast, insect, amphibian, or mammalian cells. The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

Unless otherwise stated, the term "SAA3 encoding nucleic acid" is a nucleic acid of the present invention and means a nucleic acid comprising a polynucleotide of the present invention encoding SAA3. A "SAA3 gene" is a gene of the present invention and refers to a heterologous genomic form of a full-length SAA3 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention. With respect to a protein, the term "N-terminal region" shall include approximately 50 amino acids adjacent to the amino terminal end of a protein.

As used herein "TFLK motif" shall include any formulation whether by amino acids or otherwise that would maintain the structural integrity and biological activity of the TFLK active site of SAA3.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and may be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995).

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. The BLAST programs (NCBI) and parameters used therein are used by many practitioners to align amino acid sequence fragments. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by Best-Fit program may also be used to compare sequence identity and similarity.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art i.e., conditions of stringency (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In procaryotes, yeast, and mammalian cells for example, the transforming DNA may be maintained on an episomal element such as a plasmid. With respect to eucaryotic cells, a stably transformed cell is one in which the transforming DNA has become integrated into a chromosome so that it is inherited by daughter cells through chromosome replication. This stability is demonstrated by the ability of the eucaryotic cell to establish cell lines or clones comprised of a population of daughter cells containing the transforming DNA.

A "clone" is a population of cells derived from a single cell or common ancestor by mitosis. A "cell line" is a clone of a primary cell that is capable of stable growth in vitro for many generations.

II. Description

Serum amyloid A (SAA) is an acute phase protein which is predominantly produced in the liver and occurs at elevated levels in the serum of mammals as part of the inflammatory response related to tissue injury or infection. The inventors have discovered a unique isoform of SAA, SAA3, that was thought to be nonexistent as the transcript or protein was never detected in human cells and its gene was considered nonexpressed and therefore a pseudogene.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al." are used.

A. Preparation of SAA3, Antibodies Specific for SAA3 and Nucleic Acid Molecules Encoding SAA3

1. Proteins and Antibodies

Human SAA3 may be prepared in a variety of ways, according to a variety of methods that have been developed for purifying SAA from serum which are detailed in the materials incorporated herein by reference. Variations in hydrophobic chromatography matrix systems and eluants also may be employed, such as those described by Smith et al. (Protein Expression & Purification 2: 158-161, 1991).

Alternatively, the availability of amino acid sequence information, such as SEQ ID NO: 2, enables the isolation of nucleic acid molecules encoding human SAA3. This may be accomplished using anti-human SAA3 antibodies to screen a cDNA expression library from a selected species, according to methods well known in the art. Alternatively, a series of degenerate oligonucleotide probes encoding parts or all of FIG. 2(SEQ ID NO: 1) may be used to screen cDNA or genomic libraries, as described in greater detail below.

Once obtained, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. For example, part or all of a human SAA3-encoding DNA molecule may be inserted into a vector adapted for expression in a bacterial cell (such as *E. coli*) or a yeast cell (such as *Saccharomyces cerevisiae*), or a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

Human SAA3 produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The present invention also provides antibodies from one or more selected species capable of binding to human SAA3. Polyclonal or monoclonal antibodies directed toward part or all of a selected human SAA3 may be prepared according to standard methods. Monoclonal antibodies may be prepared according to general methods of Köhler and Milstein, following standard protocols. In a preferred embodiment, antibodies are prepared, which react immunospecifically with selected epitopes of human SAA3 that distinguish it from other SAAs.

2. Nucleic Acid Molecules

Once sequence information is obtained, nucleic acid molecules encoding human SAA3 may be prepared by two general methods: (1) they may be synthesized from appropriate nucleotide triphosphates, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Nucleic acid molecules encoding human SAA3 also may be isolated from mammalian species of interest using methods well known in the art. Nucleic acid molecules from a selected species may be isolated by screening cDNA or genomic libraries with oligonucleotides designed to match a nucleic acid sequence specific to a human SAA3encoding gene. If the gene from a species is desired, the genomic library is screened. Alternatively, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning*, 1989, Cold Spring Harbor Press, Cold Spring Harbor N.Y.).

Alternatively, PCR (polymerase chain reaction) primers may be designed by the above method to encode a portion of human SAA3 protein, and these primers used to amplify nucleic acids from isolated cDNA or genomic DNA. In a preferred embodiment, the oligonucleotides used to isolate human SAA3-encoding nucleic acids are designed to encode sequences unique to human SAA3, as opposed to serum SAA.

In accordance with the present invention, nucleic acids having the appropriate sequence homology with a human SAA3-encoding nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1SSC and 1% SDS, changing the solution every 30 minutes.

One common formula for calculating the stringency conditions required to achieve hybridization between nucleic acid molecules of a specified sequence homology (Sambrook et al., 1989, supra):

$T_m = 81.5° C. + 16.6 \log[Na+] + 0.41(\% G+C) - 0.63$
(% formamide)$-600/\#bp$ in duplex As an illustration of the above formula, using [N+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. In a preferred embodiment, the hybridization is at 37° C. and the final wash is at 42° C., in a more preferred embodiment the hybridization is at 42° and the final wash is at 50°, and in a most preferred embodiment the hybridization is at 42° C. and final wash is at 65° C., with the above hybridization and wash solutions.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and wash in 0.1×SSC and 0.5% SDS at 65° C. for 15 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

Human SAA3-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting human SAA3-encoding genes or mRNA in test samples, e.g. by PCR amplification.

B. Uses of Human SAA3 Protein, Antibodies and Nucleic Acids

SAA levels may be used to diagnose or detect disease or other inflammatory conditions in a sample obtained from an animal or patients. In a preferred embodiment these levels are assayed to identify mammary infections or conditions. Elevated SAA or SAA3 levels may be associated with the acute phase and are diagnostic of infections or disease. SAA3 may also be used as a pharmaceutical as it stimulates mucin production and may be administered to alleviate intestinal problems associated with insufficient levels of the mucin, MUC 3.

1. Proteins and Antibodies

Purified human SAA3, or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected human SAA3. The full length protein or fragments of the protein may be used to advantage to generate an array of monoclonal or polyclonal antibodies specific for various epitopes of the protein, thereby providing even greater sensitivity for detection of the protein. In a preferred embodiment, fragments of human SAA3 that distinguish human SAA3 from serum SAAs are utilized for generating epitope-specific antibodies.

Polyclonal or monoclonal antibodies immunologically specific for human SAA3 may be used in a variety of assays designed to detect and quantitate the proteins. Such assays include, but are not limited to, (1) immunoprecipitation followed by protein quantification; (2) immunoblot analysis (e.g., dot blot, Western blot) (3) radioimmune assays, (4) nephelometry, turbidometric or immunochromatographic (lateral flow) assays, and (5) enzyme-coupled assays, including ELISA and a variety of qualitative rapid tests (e.g., dip-stick and similar tests).

Polyclonal or monoclonal antibodies that immunospecifically interact with human SAA3 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

2. Nucleic Acids

Human SAA3-encoding nucleic acids may be used for a variety of purposes in accordance with the present invention. The DNA, RNA, or fragments thereof may be used as probes to detect the presence of and/or expression of the genes. Methods in which human SAA3-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR) and reverse transcriptase-PCR (RT-PCR).

The exemplified human SAA3-encoding nucleic acids of the invention may also be utilized as probes to identify related genes from other species, including humans. As is well known in the art and described above, hybridization stringencies may be adjusted to allow hybridization of nucleic acid probes with complementary sequences of varying degrees of homology.

In addition to the aforementioned uses of human SAA3-encoding nucleic acids, they are expected to be of utility in the creation of transgenic cells, tissues and organisms.

The present invention provides novel purified and isolated nucleic acid sequences encoding human SAA3 protein. In presently preferred forms, the DNA sequences comprise cDNA sequences encoding the novel SAA3, or its conservatively modified variants, which are expressed in mammary epithelial cells in response to prolactin or LPS, comprise an active TFLK region and which possess the biological activity of the proteins disclosed herein. In a more preferred embodiment the nucleic acid sequence comprises at least about 80% identity to (SEQ ID NO:1) or 80% identity of the encoded amino acid sequence. Specifically, the sequence isolated is depicted in (SEQ ID NO:1). Alternate DNA forms such as genomic DNA, and DNA prepared by partial or total chemical synthesis from nucleotides as well as DNA with deletions or mutations, is also within the contemplated scope of the invention.

Further according to the invention genomic SAA3 sequences have been characterized and identified. The genomic region including introns can be used to with the human SAA3 sequences and are often necessary to achieve the most efficient expression of nucleotide sequences. The 5' region of SAA3 is also disclosed which comprises part of the promoter region and may be used to isolate the SAA3 promoter which may be used to temporal and spatial expression of heterologous genes. The promoter can provide tissue preferred expression to mammary epithelial cells and also can provide inducible expression of operably linked sequences in the presence of prolactin or LPS.

Association of DNA sequences provided by the invention with homologous or heterologous species expression control DNA sequences such as promoters, operators, regulators, and the like, allows in vivo and in vitro transcription from mRNA which, in turn, is susceptible to translation to provide the novel protein of the invention and related poly- and oligo-peptides in large quantities. In a presently preferred DNA expression system of the invention, SAA3 encoding DNA is operatively linked to a regulatory promoter DNA sequence allowing for in vitro transcription and translation of the protein.

Incorporation of DNA sequences into prokaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources. Use of mammalian host cells is expected to provide for such post-translational modifications (e.g. truncation, glycosylation, and tyrosine, serine, or threonine phosphorylation) as may be needed to confer optimal biological activity on recombinant expression products of the invention as more fully set forth hereinafter.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both prokaryotic and eucaryotic systems may be used to express human SAA3 encoding sequences; prokaryotic hosts are, of course, the most convenient for cloning procedures. Prokaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, (*Gene* (1977) 2:95). pBR322 contains genes for ampicillin and tetracycline resistance, and thus provides multiple selectable markers which can be either retained or destroyed in constructing the desired vector. Commonly used prokaryotic control sequences which are defined herein to include promoters for transcription initiation, optionally with an operator, along with ribosome binding site sequences, include such commonly used promoters as the beta-lactase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enx* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* 1972) 69:2110, or the rbCl2 method described in Maniatis, et al, *Molecular Cloning: A Laboratory Manual* (1982) Cold Spring Harbor Press, p. 254 and Hanahan, D., *J Mol Biol* (1983) 166:557-580 may be used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777-785 may be used. Transformations into yeast may be carried out according to the method of Beggs, J. D. *Nature* (1978) 275:104-109 or of Hinnen, A., et al, *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire sequence for genes or cDNA's of sizable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7y pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl2, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 μl volumes under the following standard conditions and temperatures: for example, 20 mM Tris-Cl pH 7.5, 10 mM $MgCl_2$, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per µg of vector at 60° C. for about one hour. In order to recover the nucleic acid fragments, the preparation is extracted with phenol/chloroform and ethanol precipitated. Alternatively, re-ligation can be prevented in vectors which have been double digested by additional restriction enzyme digestion and/or separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487-6500 and Adelman, J. P., et al, DNA (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct ligations for plasmid construction can be confirmed by first transforming *E. coli* strain MC1061 (Casadaban, M., et al, *J Mol Biol* (1980) 138:179-207) or other suitable host with the ligation mixture. Successful transformants are selected by ampicillin, tetracycline or other antibiotic resistance by using other markers depending on the mode of plasmid construction, as is understood in the art. Plasmids from the transformants are then prepared according to the method of Clewell, D. B., et al, *Proc Natl Acad Sci* (*USA*) (1969) 62:1159, optionally following chloramphenicol amplification (Clewell, D. B., *J Bacteriol* (1972) 110: 667). Several mini DNA preps are commonly used, e.g., Holmes, D. S., et al, *Anal Biochem Acids Res* (1979) 7:1513-1523. The isolated DNA is analyzed by restriction and/or sequenced by the dideoxy nucleotide method of Sanger, F., et al, *Proc Natl Acad Sci* (*USA*) (1977) 74:5463 as further described by Messing, et al, *Nucleic Acids Res* (1981) 9:309, by the method of Maxam, et al, *Methods in Enzymology* (1980) 65:499.

Hosts Exemplified

Host strains used in cloning and prokaryotic expression herein are as follows:

For cloning and sequencing, and for expression of construction under control of most bacterial promoters, *E. coli* strains such as MC1061, DH1, RR1, C600hfl, K803, HB101, JA221, and JM101 can be used.

3. Additional Uses Based on the Discovery of SAA3

Human SAA3 also may be used for a variety of other purposes. These include, but are not limited to its use as (1) a carrier for delivery of molecules across the gut or vasculature, (2) a nutritional supplement for development of the gut mucosa in newborns, and (3) as a regulator of immune responses (via injection or oral administration).

4. Pharmaceutical Preparations

According to the invention SAA3 and more particularly an active site(s), (i.e. the TFLK motif) stimulate mucin production in the intestine. This is significant as mucins have been shown to have a key role in the prevention and treatment of intestinal infections and many probiotics act through inducing mucin production. See Mack et al, "Probiotics inhibit enteropathogenic *Escherechia coli* adherence in vitro by inducing intestinal mucin gene expression", 1999, Am J Physiol, 276:G941-950, the disclosure of which is incorporated herein by reference. Thus the invention also includes pharmaceutical preparations for humans and animals involving human SAA3. Those skilled in the medical arts will readily appreciate that the doses and schedules of pharmaceutical composition will vary depending on the age, health, sex, size and weight of the human and animal rather than administration, etc. These parameters can be determined for each system by well-established procedures and analysis e.g., in phase I, II and III clinical trials.

For administration, the SAA3 can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, drageemaking, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers.

In addition to administration with conventional carriers, active ingredients may be administered by a variety of specialized delivery drug techniques which are known to those of skill in the art. The following examples are given for illustrative purposes only and are in no way intended to limit the invention.

As used herein the term "an effective amount" shall mean an amount of human SAA3 sufficient to increase mucin production so that adherence of pathogens to mucosal cells is decreased as determined by the methods and protocols disclosed herein.

According to the invention, the novel human SAA3 and more particularly its TFLK motif active site has been shown to stimulate mucin production, more specifically MUC3. Mucin production has been shown to inhibit the adherence of E coli, and probiotic agents which do the same, have been shown to work through stimulation of mucins. The human SAA3 and/or peptide can be used in place of a probiotic.

The significance of mucins in intestinal infections lies in their ability to prevent the events necessary for infectious organisms to cause disease.

Mucins are produced by intestinal epithelial cells and secreted onto their surface. Thus, mucins are strategically located between the epithelial cells of the gut and offending agents ingested into the intestinal tract (i.e. infectious agents, noxious substances).

Mucins also inhibit the adherence of bacteria to the epithelial cells of the intestinal tract. Binding of bacteria to the lining cells of the gut is the first step in invasion, toxin delivery and development of diarrheal disease. If binding of the enteric pathogens is inhibited then disease does not develop.

Mucins have been shown to inhibit replication of viruses.

Mucins are part of innate immunity and a basic defense system of the gut. Thus, in comparison to the antibody/T-cell driven acquired immune system, mucins provide advantages including: immediate or rapidly inducible response to offending agents, broad spectrum of action, locally effective, and conserved across the animal kingdom.

Increased mucin secretion due to infectious agents is a well-known clinical phenomenon. Mucin inhibits infectious intestinal bacteria from attaching to intestinal cells and thus, prevents infection. This is accomplished by mucins attaching to the structures on the wall of the bacteria that would normally be used to attach to the intestinal cells. Probiotic bacteria (non-infectious bacteria) prevent attachment of infectious intestinal bacteria to epithelial cells lining the intestinal tract. Secreted material from probiotic bacteria cause intestinal cells to produce more mucin and one mechanism whereby probiotic agents prevent infection.

This demonstrates pharmaceutical applications of this peptide for numerous enteric pathologies. For example the prevention of traveler's diarrhea. Many infectious organisms are geographical in nature and travelers outside of their own areas have usually not been previously exposed to these organisms, thus have not developed immunity to them. Many people will take antibiotics before traveling, but some antibiotics have deleterious side effects and also organisms are becoming resistant to many antibiotics.

Another potential use would be to prevent dysentery and other infectious diseases particularly for the military. Human SAA3 is a rapid, safe and effective means to reduce or prevent intestinal-related infections.

Another example includes prevention or treatment of infant diarrhea. Breast fed infants have far fewer infections than formula fed infants. Since colostrum is a natural substance which is beneficial to the infant and human SAA3 is a component of colostrum, it will be an invaluable natural addition to formula. Such formulas are commonly commercially available such as Infamel™, Similac™, Carnation Good Start™, and Gerber™. Probiotics have been shown to reduce severity and shorten the recovery time for viral caused diarrhea. Thus, another use for human SAA3 would be for children with this condition which would also have an economic impact by reducing hospital stays and costs.

Yet another example includes the prevention or treatment of necrotizing enterocolitis (NEC). This is a serious complication that occurs in premature infants. With the various reproduction techniques that are being used there has been an explosion in the number of premature infants. Therapy for NEC has remained the same for the last few decades. Since bacteria in the gut of the premature infant have a major role in the development of NEC, therapy for this condition consists of keeping the infant from feeding, giving strong antibiotics and hoping that the bowel does not perforate.

Another use for human SAA3 includes the prevention of diarrhea in areas of outbreaks. *E. coli* 0157:H7 outbreaks can lead to deaths from hemolytic-uremic syndrome. SAA3 induces mucin production which prevents *E. coli* from adhering to epithelial cells and thus could prevent this infection.

Yet another example includes the treatment or prevention of urinary tract infections. The bladder epithelial cells are very similar to intestinal epithelial cells and are capable of producing mucins. Therefore prevention of urinary infections, including hospitalized patients with urinary catheters, would also be a use for the pharmaceutical compositions of the invention.

Although this disclosure includes upregulation of intestinal mucins, epithelial cells lining other mucosal surfaces, (e.g. nasopharynx, bladder, etc.), also produce mucins. These mucins function to prevent infections analogous to intestinal mucins, and would also be effective targets for treatment according to the invention.

The following examples are provided to describe the invention in greater detail. They are intended to illustrate, not to limit, the invention.

EXAMPLES

Cell line and culturing. The human mammary gland epithelial cell lines MCF-7 (ATCC) and T47-D (ATCC) were used in this study. These human mammary epithelial cells were chosen since both of these cell lines have been determined to express prolactin (PRL) receptors (E. Canbay, M. Norman, E. Kilic, V. Goffin, I. Zachary, Prolactin stimulates the JAK2 and focal adhesion kinase pathways in human breast carcinoma T47-D cells, Biochem. J. 324 (1991) 231-236). MCF-7 cells were grown in Dulbecco's Modified Eagle's Medium (DMEM) supplemented with 0.2 U/mL insulin, 2 mM glutamine, 4.5 g/L glucose, 50 μg/mL streptomycin, 50 U/mL penicillin, and 10% FBS. T47-D cells were cultured in RPMI 1640 medium supplemented as was described for the MCF-7 cells except 10 mM HEPES and 1 mM sodium pyruvate were also added. Cell cultures were incubated at 37° C. in a humidified atmosphere with 5% $CO_2$. For cell culture passage, adherent cells were released by using trypsin-EDTA (Invitrogen Corp.).

Cell stimulation assays. To detect M-SAA3 expression, these human mammary gland cells were stimulated with either 100 ng/mL of human recombinant prolactin (PRL) (Sigma) or 20 μg/mL of *Escherichia coli* lipopolysaccharide (LPS) (Difco) for 0 h, 0.5 h, 4 h, 24 h, and 48 h. For the LPS induced mammary cells, the cells were grown to confluence and then stimulated with LPS in DMEM, supplemented as above except containing 1 μg/mL hydrocortisone and only 2% FBS. For the PRL stimulated mammary gland cells, the cells were grown to 85% confluence on wells coated with MATRIGEL Matrix (BD Biosciences) and then induced with PRL in a serum-free 1:1 mixture of DMEM and F 12 medium supplemented as previously described (E. Canbay, M. Norman, E. Kilic, V. Goffin, I. Zachary, Prolactin stimulates the JAK2 and focal adhesion kinase pathways in human breast carcinoma T47-D cells, Biochem. J. 324 (1991) 231-236). The concentration of PRL used in this study was based on physiological levels of PRL during lactation in humans that is typically between 100-200 ng/mL, whereas basal levels are within the range of 2-15 ng/mL (M. C. Neville, J. Morton, Physiology and endocrine changes underlying human lactogenesis II, J. Nutr. 131 (2001) 3005S-3008S). For the 48 h stimulation, the medium was replaced after 24 h with fresh medium containing the appropriate components and stimulant.

RNA isolation and RT-PCR. Total RNA was isolated from either unstimulated or stimulated mammary gland epithelial cells using TRIZOL (Invitrogen Life Technologies), as described by the manufacturer. The RNA was concentrated by ethanol precipitation and stored at −80° C. RNA integrity was visualized by fractionation in a 1% (wt/vol) agarose gel and subsequent staining of the gel with ethidium bromide. First strand cDNA synthesis was performed using 5 μg of total RNA, 40 μM of a poly $d(T)_{14}$ oligonucleotide, and SuperScript II RNase H⁻ Reverse Transcriptase (Invitrogen Life Technologies) according to the manufacturer's recommendations. Second strand cDNA synthesis and amplification of the double stranded cDNA was performed with AmpliTaq Gold DNA Polymerase (Applied Biosystems). The forward F1 and reverse R1 primers (Table 1) used in second strand cDNA synthesis are complementary to the proposed antisense strand of exon 2 and sense strand of exon 3 for the predicted human SAA3 cDNA sequence (GenBank accession number X13895), respectively.

TABLE 1

Human SAA3-specific oligonucleotide primers used to obtain human M-SAA3 cDNA.

| | Oligonucleotide sequence | *bp # | |
|---|---|---|---|
| RT-PCR primer | | | |
| F1 | 5'-GATGAAGCTCTCCACTGGCATCA-3' | 56 bp | SEQ ID NO: 5 |
| R1 | 5'-TCAGAGTAGGCTCTCCACATGTCTT-3' | 154 bp | SEQ ID NO: 6 |
| F4 | 5'-AACTTGAAACAGAATGTGTATTATCCTTGGTTG-3' | 1 bp | SEQ ID NO: 7 |
| RACE primer | | | |
| R3 (1° 5'RACE) | 5'-CAGCTGCCTTGAGGAATGTTAACCAT-3' | 116 bp | SEQ ID NO: 8 |
| R4 (2° 5'RACE) | 5'-GCTGCTGACACCCAGGACCAG-3' | 90 bp | SEQ ID NO: 9 |
| F1b (1° 3'RACE) | 5'-AGCAGGATGAAGCTCTCCTCTGGCATCA-3' | 51 bp | SEQ ID NO: 10 |
| F2c (2° 3'RACE) | 5'-CAGCCAAGGATGGTTAACATTCCTCAAGGCA-3' | 107 bp | SEQ ID NO: 11 |

*(bp # corresponds to the location of the primer in FIG. 2 relative to the 5' nucleotide for the human M-SAA3 cDNA sequence obtained in this study.)

The cycling parameters using a GeneAmp PCR System 2700 thermocycler (Applied Biosystems) were 1 cycle for 10 min. at 95° C., 43 cycles for 30 seconds at 94° C., 40 seconds at 60° C., and 20 seconds at 60° C., followed by 1 cycle for 10 min. at 60° C. The resulting 123 bp RT-PCR product obtained following stimulation with either LPS or PRL was cloned into pCRII-TOPO (Invitrogen Life Technologies). The cloned inserts were sequenced in both directions to confirm identity. Control RT reactions containing forward and reverse primers that would amplify a 390 bp glyceraldehyde-3-phosphate dehydrogenase (GAPDH) cDNA fragment were also performed with each cDNA preparation to ensure that no mRNA degradation occurred.

5' and 3' Rapid Amplification of cDNA Ends. Full-length M-SAA3 cDNA was obtained by 5' and 3' rapid amplification of cDNA ends (RACE) using the commercially available 5' RACE and GeneRacer Systems (Invitrogen Life Technologies) as recommended by the manufacturer. Briefly, 5 µg of total RNA from both unstimulated and stimulated mammary gland epithelial cells was reverse transcribed using the gene-specific reverse R1 primer for 5' RACE and the poly d(T)$_{18}$ GeneRacer adapter primer (Invitrogen Life Technologies) for the 3' GeneRacer procedures. Gene-specific RACE primers for nested primary and secondary PCR were designed according to the manufacturer's recommendations and were complementary to selected regions of the 123 bp middle M-SAA3 cDNA fragment described above. The nested primary and secondary PCR primers used in the 5' and 3' RACE procedures are shown in Table 1. Primary PCRs were carried out in 50 µL volumes containing 1 µL of first strand cDNA. The thermal cycling parameters used in the primary PCRs were 1 cycle for 9 min. at 95° C.; 5 cycles for 30 seconds at 94° C. and 1.5 min. at 72° C.; 5 cycles for 30 seconds at 94° C. and 1.5 min. at 70° C.; 25 cycles for 30 seconds at 94° C., 1 min. at 65° C., and 1.5 min. at 72° C.; and then 1 cycle for 10 min. at 72° C. Secondary PCRs were carried out in 50 µL volumes containing 1 µL of the appropriate primary PCR mixture, adapter primer, and either the forward or reverse nested secondary gene-specific primer. The thermal cycling parameters were the same as those used for primary PCR except 33 cycles instead of 25 cycles for the fourth cycling parameter was utilized. The resulting secondary PCR amplicons were sequenced to confirm identity and to obtain the full-length human M-SAA3 cDNA sequence.

Nucleotide sequence analysis of M-SAA3. The cloned 123 bp RT-PCR amplicon was sequenced using the vector-based Sp6 and T7 primers and the secondary 5' and 3' RACE products were sequenced using the gene-specific nested secondary primers. The DNA sequence was analyzed using the BESTFIT and PILEUP programs in the Wisconsin Genetics Computer Group (GCG) Package (Version 10.2). The nucleotide sequence for M-SAA3 cDNA was deposited in the GenBank database under accession number AY209188.

Induction and detection of M-SAA3 expression. To determine if SAA3 was expressed following PRL or LPS stimulation of human mammary gland epithelial cells, RT-PCR was performed with the SAA3-specific F1 and R1 primers (Table 1). Control RT reactions containing forward and reverse primers complementary to GAPDH cDNA amplified the expected 390 bp RT-PCR product for each cDNA preparation, ensuring that the mRNA used to prepare the cDNA was of high integrity (FIG. 1). RT-PCR with the SAA3-specific F1 and R1 primers and the cDNA prepared from human MCF-7 mammary gland cells stimulated with either PRL for 0.5 h, 4 h, or 24 h or LPS for 48 h resulted in an amplicon that was 123 bp in length. FIG. 1 shows the 123 bp RT-PCR product obtained with the SAA3-specific F1 and R1 primers and the cDNA prepared from mammary cells stimulated for either 0.5 h with PRL or 48 h with LPS. Also shown in FIG. 1, the cDNA prepared from unstimulated mammary gland cells did not result in a detectable amplicon with the SAA3-specific F1 and R1 primers. The presence of the 123 bp product was detected by RT-PCR with the SAA3-specific F1 and R1 primers and cDNA prepared from MCF-7 cells as early as 0.5 h after LPS stimulation and was consistently detected after 48 h. Since the MCF-7 cells on the matrix became too non-adherent following stimulation with PRL for 48 h, cDNA was not prepared from this time point.

Sequencing of the 123 bp RT-PCR product obtained with the SAA3-specific F1 and R1 primers and cDNA prepared from either the PRL or LPS stimulated MCF-7 cells revealed 97% identity to a region in the human SAA3 cDNA sequence originally predicted by Sack and Talbot (G. H. Sack, C. C. Talbot, Jr., The human serum amyloid A (SAA)-encoding gene GSAA1: nucleotide sequence and possible autocrine-collagenase-inducer function, Gene 84 (1989) 509-515). The nucleotide sequence of this mammary-associated SAA3 (M-SAA3) 123 bp RT-PCR product is shown in FIG. 2, along with the flanking nucleotides that comprise the full-length cDNA sequence for human M-SAA3. The M-SAA3 123 bp RT-PCR fragment contained a splice junction in which a 2692 nucleotide intron was precisely spliced out, as was predicted by Sack and Talbot (G. H. Sack, C. C. Talbot, Jr., The human serum amyloid A (SAA)-encoding gene GSAA1: nucleotide sequence and possible autocrine-collagenase-inducer function, Gene 84 (1989) 509-515). The presence of this intron in the human SAA3 gene was confirmed by performing PCR with the SAA3-specific F1 and R1 primers and human genomic DNA as the template. The absence of this intron confirmed that the RT-PCR product was generated from M-SAA3 mRNA and not genomic DNA contamination. The 123 bp M-SAA3 cDNA product was also detected in the cDNA preparations that derived from the stimulated T47-D human mammary gland cell line.

Isolation and analysis of full-length human M-SAA3 cDNA. To obtain the full-length M-SAA3 cDNA, 5' and 3' rapid amplification of cDNA ends (RACE) was performed using RNA isolated from PRL or LPS stimulated mammary MCF-7 cells. The resulting 150 bp 5' RACE and 550 bp 3' GeneRacer RACE products obtained from secondary PCR with the M-SAA3 specific nested secondary primers were sequenced. Both secondary PCR products from the RACE procedures overlapped with the sequence of the 123 bp M-SAA3 middle cDNA fragment. Similar to the initial 123 bp RT-PCR product, these secondary PCR amplicons were only detected with the cDNA preparations from either the PRL or LPS stimulated MCF-7 mammary cells. To ascertain that the 5' RACE secondary PCR product derived from M-SAA3 mRNA and not genomic DNA, the M-SAA3-specific forward F4 and reverse R1 primers (Table 1) were used in RT-PCR. The resulting 178 bp M-SAA3 cDNA fragment did not contain the first intron as expected, providing evidence that this 5' RACE secondary PCR product was indeed part of the 5' region of the M-SAA3 transcript. Similarly, the 3' RACE product obtained in secondary PCR did not contain the last intron in M-SAA3 cDNA. Together these results further verified that the RT-PCR and secondary RACE products were derived from M-SAA3 mRNA and not genomic DNA. Moreover, these amplicons were only detectable in the cDNA preparations that originated from either the PRL or LPS stimulated mammary gland cells, confirming that these stimulants induce transcriptional expression of the human M-SAA3 gene.

The complete nucleotide sequence obtained for human M-SAA3 cDNA following either PRL or LPS stimulation was 655 bp in length and is shown in FIG. 2. Also shown in FIG. 2 is a comparison of the human M-SAA3 cDNA obtained in this study with the proposed human SAA3 cDNA sequence predicted by Sack and Talbot (G. H. Sack, C. C. Talbot, Jr., The human serum amyloid A (SAA)-encoding gene GSAA1: nucleotide sequence and possible autocrine-collagenase-inducer function, Gene 84 (1989) 509-515) (GenBank accession no. X13895) (SEQ ID NO:3). Unlike the four-exon structure of the other three human SAA genes, the M-SAA3 gene has a three-exon structure. The region originally predicted by Sack and Talbot to be exon 1 is not present in the human M-SAA3 cDNA, nor is the initially predicted intron 1 entirely spliced out. Rather, the 5' untranslated region (UTR) contains the last 52 nucleotides originally predicted to be part of intron 1. The 5' region of M-SAA3 cDNA contains a reasonable Kozak consensus sequence with the most probable translational initiation codon located at nucleotides 57-59 (M. Kozak, Structural features in eukaryotic mRNAs that modulate the initiation of translation, J. Biol. Chem. 266 (1991) 19867-19870).

Our results showed that the first intron of the human SAA3 gene is 2692 nucleotides in length in agreement with the several genomic DNA sequences deposited in GenBank (Accession numbers AC055860.13 and AC108007.5). This intron was originally predicted by Sack and Talbot (G. H. Sack, C. C. Talbot, Jr., The human serum amyloid A (SAA)-encoding gene GSAA1: nucleotide sequence and possible autocrine-collagenase-inducer function, Gene 84 (1989) 509-515) to be intron 2 and 2638 nucleotides in length in the human SAA3 gene (GenBank accession no. X13895). The M-SAA3 cDNA obtained in this study indicates that the splice site junction for intron 1 concurs with the prediction made by Sack and Talbot (G. H. Sack, C. C. Talbot, Jr., The human serum amyloid A (SAA)-encoding gene GSAA1: nucleotide sequence and possible autocrine-collagenase-inducer function, Gene 84 (1989) 509-515) for intron 2. The last intron in M-SAA3, intron 2, is 321 bp in length. The processing of this intron from M-SAA3 mRNA was similar, but not identical to the initially predicted 273 bp intron located in this region that was presumed to be intron 3. More specifically, the last or third exon of M-SAA3 contained an additional 71 nucleotides originally thought to be part of intron 3. Further comparisons of the human M-SAA3 cDNA obtained in this study with the human SAA3 gene sequence deposited in GenBank (accession no. X13895) also indicated that both intron 1 and intron 2 conform to the GT-AG consensus sequence for splice donor/acceptor sites.

The presence of a single base (T) insertion at nucleotide 204 of the human M-SAA3 cDNA results in a frameshift and an earlier translational stop codon than was originally predicted for the gene product encoded by human SAA3 (SEQ ID NOS:3 and 4) (G. H. Sack, C. C. Talbot, Jr., The human serum amyloid A (SAA)-encoding gene GSAA1: nucleotide sequence and possible autocrine-collagenase-inducer function, Gene 84 (1989) 509-515) (FIG. 2). This single base (T) insertion supports the results obtained in previous studies (B. Kluve-Beckerman, M. L. Drumm, M. D. Benson, Nonexpression of the human serum amyloid A three (SAA3) gene, DNA Cell Biol. 10 (1991) 651-661; (G. C. Sellar, A. S. Whitehead, Localization of four human serum amyloid A (SAA) protein superfamily genes to Chromosome 11p: Characterization of a fifth SAA-related gene sequence, Genomics 16 (1993) 774-776) and concurs with a contig for this region of the human genome available from The Sangre Centre human genome sequencing project (www.ensembl.org/genome/central). Hence, the resulting 3' UTR is 406 bp in length rather than 145 bp 3' UTR originally predicted for human SAA3 cDNA. As shown in FIG. 2, several additional nucleotide differences were also detected between the human M-SAA3 cDNA sequence obtained in this study and the predicted SAA3 cDNA, four of which alter the predicted residue encoded by the cognate codon. However, the polyadenylation signal (AAUAAA) in the M-SAA3 transcript, positioned 21 nucleotides upstream of the poly (A) tail, corroborates with the prediction made by Sack and Talbot for the location of this consensus sequence in the human SAA3 gene (G. H. Sack, C. C. Talbot, Jr., The human serum amyloid A (SAA)-encoding gene GSAA1: nucleotide sequence and possible autocrine-collagenase-inducer function, Gene 84 (1989) 509-515).

Comparison of human M-SAA3 with other SAA3 isoforms. Human M-SAA3 cDNA contained an open reading frame that would conceptually translate into a 60 amino acid precursor protein containing an 18 residue signal peptide typically found in other SAA proteins (FIG. 3). The mature 42 amino acid protein would have a calculated molecular mass of 4866.69 daltons and a theoretical pI of 9.31. As shown in FIG. 3, sequence alignment of the predicted human M-SAA3 protein with rabbit, hamster, bovine, and mouse SAA3 isoforms shows considerable amino acid identity (~94%) for the first 48 N-terminal residues. However, the nucleotide insertion at base 204 in the human M-SAA3 transcript generates a downstream translational stop codon at codon 61 of the precursor protein, thus resulting in a smaller protein than the othermammalian SAA3 isoforms (FIG. 3). The predicted residue encoded at this base insertion at codon 50, as well as the following amino acids in the human SAA3 precursor protein, also differ significantly from the amino acids in this region of other mammalian SAA3 isoforms (FIG. 3). In addition, these C-terminal eleven amino acids of human SAA3 and three residues located prior to the nucleotide insertion at codon 50 of the precursor protein differ from the previously reported sequence for human SAA3 (Genbank accession no. X13895) (SEQ ID NOS:3 and 4).

Regulation of human M-SAA expression. The hormone PRL and the endotoxin LPS, an outer membrane component from gram-negative bacteria, were shown in this study to stimulate human M-SAA3 expression. In human and animals, LPS signals the presence of a gram-negative bacterial infection. LPS, a major mediator of endotoxin shock (E. T. Rietschel, T. Kirikae, F. U. Schade, U. Mamat, G. Schmidt, H. Loppnow, A. J. Ulmer, U. Zahringer, U. Seydel, F. D. Padowa, M. Schreier, H. Brade, Bacterial endotoxin: molecular relationships of structure to activity and function, FASEB J. 8 (1994) 217-225) has been shown to stimulate primary cultures of mammary epithelial cells from lactating cows to produce the inflammatory cytokines IL-1 and IL-6 in a dose dependent manner in vitro (H. Okada, H. Ohtsuka, S. Kon-nai, R. Kirisawa, Y. Yokomizo, T. Yoshino, T. J. Rosol, Effects of lipopolysaccharide on production of interleukin-1 and interleukin-6 by bovine mammary epithelial cells in vitro, J. Vet. Med. Sci. 61 (1999) 33-35). These mammary cells were also shown to express the inflammatory cytokine TNF-α transcript (H. Okada, T. Ito, H. Ohtsuka, R. Kirisawa, H. Iwai, K. Yamashita, T. Yoshino, T. J. Rosol, Detection of interleukin-1 and interleukin-6 on cryopreserved bovine mammary epithelial cells in vitro, J. Vet. Med. Sci. 59 (1997) 503-507). Likewise, human primary cultures of mammary epithelial cells have also been shown to produce IL-6 and TNF-α (F. Basolo, P. G. Conaldi, L. Fiore, S. Calvo, A. Toniolo, Normal breast epithelial cells produce interleukins 6 and 8 together with tumor-necrosis factor; defective IL6 expression in mammary carcinoma, Int. J. Cancer 55 (1993) 926-930). The inflammatory cytokines IL-1; IL-6, and TNF-α are known to activate expression of SAA genes in specific contexts and define the magnitude of the immune response. Interestingly, the human SAA3 promoter contains four putative acute phase response factor (APRF) consensus binding sites (CTGGGA) (SEQ ID NO:12), suggesting that endotoxins such as LPS may induce expression of inflammatory cytokines which then stimulate M-SAA3 expression.

Another inducer of M-SAA3 expression is PRL. This multifunctional hormone regulates a wide spectrum of physiological processes including mammary gland development, lactation, and immune function by endocrine, paracrine, and/or autocrine mechanisms (M. C. Neville, J. Morton, Physiology and endocrine changes underlying human lactogenesis II, J. Nutr. 131 (2001) 3005S-3008S). At the molecular level, PRL induces homodimerization of the PRL receptor, a member of the hematopoietin/cytokine receptor superfamily that is found on numerous cells including mammary gland cells (E. Canbay, M. Norman, E. Kilic, V. Goffin, I. Zachary, Prolactin stimulates the JAK2 and focal adhesion kinase pathways in human breast carcinoma T47-D cells, Biochem. J. 324 (1991) 231-236; C. Bole-Feysot, V. Goffin, M. Edery, N. Binart, P. A. Kelly, Prolactin (PRL) and its receptor: actions, signal transduction pathways and phenotypes observed in PRL receptor knockout mice, Endocr. Rev. 19 (1998) 225-268). This initiates the activation of the receptor-associated tyrosine-specific kinase, JAK, and the subsequent activation of signal transducers and activators of transcription (STATs). STAT3 has been determined to induce the expression of a variety of acute phase genes in response to inflammation and tissue injury (J. N. Ihle, STATs: signal transducers and activators of transcription, Cell 84 (1996) 331-334). The regulation of STAT5 in vitro and in vivo indicates that this factor has a central and significant role in the lactogenic hormone signaling pathway (B. Groner, F. Gouilleux, Prolactin-mediated gene activation in mammary epithelial cells, Curr. Opin. Genet. Dev. 5 (1995) 587-594) and upregulates the expression of milk proteins in mammary tissue in response to PRL (J. N. Ihle, STATs: signal transducers and activators of transcription, Cell 84 (1996) 331-334). Interestingly, the promoter region of human SAA3 (GenBank Accession No. X13895) contains a putative STAT3-(TTCC(G=C)GGAA) (SEQ ID NO:13) and STAT5-like binding site (TTCC(A>T)GGAA) (SEQ ID NO:14) positioned at 1607 bp (TTCCCGGAA) (SEQ ID NO:15) and 429 bp (TTCCAAGGAA) (SEQ ID NO:16) upstream of the 5' UTR, respectively. These cis-acting elements may be responsible in part for the upregulation of M-SAA3 transcriptional expression following either LPS or PRL stimulation. PRL induced activation of STAT5 in human mammary epithelial cell lines has been previously reported (E. Canbay, M. Norman, E. Kilic, V. Goffin, I. Zachary, Prolactin stimulates the JAK2 and focal adhesion kinase pathways in human breast carcinoma T47-D cells, Biochem. J. 324 (1991) 231-236). Although IL-6 has been shown to activate the JAK/STAT pathway in human mammary epithelial cells (A. Badache, N. E. Hynes, Interleukin 6 inhibits proliferation and, in cooperation with an epidermal growth factor receptor autocrine loop, increases migration of T47D breast cancer cells, Cancer Res. 61 (2001) 383-391), the influence of LPS on STAT factor activation in human mammary epithelial cells is currently unknown.

Although the precise biological function(s) of SAA has not been determined, several studies suggest that the N-terminal region of the various SAA isoforms is responsible in part for their structural and functional properties. For example, the N-terminal region of A-SAA1 and A-SAA2 specifically binds and transports cholesterol into HepG2 liver and aortic smooth muscle cells, suggesting a plausible role of cholesterol flux modulation by A-SAA1 and A-SAA2 during an acute phase response, as well as in atherosclerosis (J. Liang, B. M. Schreiber, M. Salmona, G. Phillip, W. A. Gonnerman, F. C. de Beer, J. D. Sipe, Amino terminal region of acute phase, but not constitutive, serum amyloid A (apoSAA) specifically binds and transports cholesterol into aortic smooth muscle and HepG2 cells, J. Lipid Res. 37 (1996) 2109-2116). Other studies demonstrated that the N-terminal region of A-SAA is the precursor for amyloid A, a chief constituent of amyloid fibrils found in secondary amyloidosis (A. Husebekk, B. Skogen, G. Husby, G. Marhaug, Transformation of amyloid precursor SAA to protein AA and incorporation in amyloid fibrils in vivo, Scand. J. Immunol. 21 (1985) 283-287; J. J. Liepnieks, B. K. Beckerman, M. D. Benson, Characterization of amyloid A protein in human secondary amyloidosis: the predominant deposition of serum amyloid A1, Biochim. Biophys. Acta 1270 (1995) 81-86). We have previously isolated the M-SAA3 isoform from the colostrum of several mammals (T. L. McDonald, M. A. Larson, D. R. Mack, A. Weber, Elevated extrahepatic expression and secretion of mammary-associated serum amyloid A 3 (M-SAA3) into colostrum, Vet. Immunol. Immunopathol. 83 (2001) 205-213). Moreover, pretreatment of human intestinal epithelial cells with the synthetic N-terminal ten amino acids of M-SAA3 stimulates production of the protective intestinal mucin MUC3 and significantly reduces enteropathogenic *Escherichia coli* (EPEC) adherence to these cells, relative to untreated cells (D. R. Mack, T. L. McDonald, M. A. Larson, S. Wei, A. Weber, The conserved TFLK motif of mammary-associated serum amyloid A3 is responsible for upregulation of intestinal MUC3 mucin expression in vitro, Pediatr. Res. 53 (2003) 137-142; M. A. Larson, S. H. Wei, A. Weber, D. R. Mack, T. L. McDonald, Human mammary-associated serum amyloid A3 peptide enhances intestinal MUC3 expression and inhibits EPEC adherence, Biochem. Biophys. Res. Comm. 300 (2003) 531-540). Together these studies ascribe function to the various SAA isoforms based on their composition, structure, and site of expression or localization, all of which contribute to either a positive or negative outcome.

References. All references cited herein are hereby expressly incorporated herein by reference. This includes the following published applications and patents, U.S. Pat. No. 6,509,444, WO01/31006, and PCT/US99/19428, M. A. Larson, A. Weber, A. T. Weber, T. L. McDonald, Differential expression of bovine mammary-associated serum amyloid A3 is induced by prolactin or lipopolysaccharide, (in preparation).

G. Ramadori, J. D. Sipe, H. R. Colten, Expression and regulation of the murine serum amyloid A (SAA) gene in extrahepatic sites, J. Immunol. 135 (1985) 3645-3647.

R. L. Meek, E. P. Benditt, Amyloid A gene family expression in different mouse tissues, J. Exp. Med. 164 (1986) 2006-2017.

R. L. Meek, E. P. Benditt, Rat tissues express serum amyloid A protein-related mRNAs, Proc. Natl. Acad. Sci. USA 86(1989) 1890-1894.

What is claimed is:

1. An isolated nucleic acid molecule, said molecule encoding an SAA3 protein wherein said nucleic acid molecule comprises a nucleotide sequence comprising the sequence set forth in SEQ ID NO: 1 that encodes a protein with the biological activity of said SAA3 protein.

2. A vector comprising the nucleic acid molecule of claim 1.

3. A host cell transformed with the vector of claim 2.

4. The host cell of claim 3 wherein said host cell is a bacterial cell.

5. The host cell of claim 3 wherein said host cell is an animal cell.

6. The host cell of claim 5, wherein said animal cell is from a *Homo sapien*.

7. The host cell of claim 5 wherein said animal cell is a mammary cell.

8. A nucleotide construct comprising: a nucleic acid molecule of claim 1, wherein said nucleic acid molecule is operably linked to a promoter that drives expression in a host cell.

9. The isolated nucleic acid molecule of claim 1 wherein said SAA3 biological activity is stimulation of mucin 3 (MUC3) production in mammary epithelial cells.

* * * * *

SEQUENCE LISTING

<160> NUMBER OF SEQ ID NOS: 16

<210> SEQ ID NO 1
<211> LENGTH: 655
<212> TYPE: DNA
<213> ORGANISM: Homo sapiens
<220> FEATURE:
<221> NAME/KEY: CDS
<222> LOCATION: (57)..(236)
<223> OTHER INFORMATION:

<400> SEQUENCE: 1

```
aacttgaaac agaatgtgta ttatccttgg ttgtgtttcc ttggccctgc agcagg atg      59
                                                              Met
                                                                1 aag ctc tcc tct ggc atc att ttc tgc tcc ctg gtc ctg ggt gtc agc     107
Lys Leu Ser Ser Gly Ile Ile Phe Cys Ser Leu Val Leu Gly Val Ser
      5                  10                  15 agc caa gga tgg tta aca ttc ctc aag gca gct ggc caa ggg act aaa     155
Ser Gln Gly Trp Leu Thr Phe Leu Lys Ala Ala Gly Gln Gly Thr Lys
 20                  25                  30 gac atg tgg aaa gcc tac tct gac atg aaa gaa gcc aat tac aaa aaa     203
Asp Met Trp Lys Ala Tyr Ser Asp Met Lys Glu Ala Asn Tyr Lys Lys
 35                  40                  45 ttc aga caa ata ctt cca tgc ttg ggg gaa cta tgatgctgta caaggggggc   256
Phe Arg Gln Ile Leu Pro Cys Leu Gly Glu Leu
50                  55                  60 ttggggctgt ctgggctaca gaagtgatca ggtaatgcac attcctgatg ttgccaggaa   316
tgagtgagca gagcttgact gccttggaca gtcaggagag agcgatgcca gagagaacgt   376
ccagagactc acaggagacc atgcagagga ttcgctggct ggccaggcta ccaacaaatg   436
gggccagagt ggcaaagacc ccaatcactt ccgacctgct ggcctgccag agaaatactg   496
agcttccttt tcaatctgct ctcaggagac ctggctgtga gccctgagg gcagggacat    556 ttgttgacct acagttactg aattctatat ccctagtact tgatatagaa cacataaaaa   616
tgcttaataa atgcttgtga atccaaaaa aaaaaaaaa                           655
```

<210> SEQ ID NO 2
<211> LENGTH: 60
<212> TYPE: PRT
<213> ORGANISM: Homo sapiens

<400> SEQUENCE: 2

```
Met Lys Leu Ser Ser Gly Ile Ile Phe Cys Ser Leu Val Leu Gly Val
  1               5                  10                  15

Ser Ser Gln Gly Trp Leu Thr Phe Leu Lys Ala Ala Gly Gln Gly Thr
             20                  25                  30

Lys Asp Met Trp Lys Ala Tyr Ser Asp Met Lys Glu Ala Asn Tyr Lys
         35                  40                  45

Lys Phe Arg Gln Ile Leu Pro Cys Leu Gly Glu Leu
     50                  55                  60
```

<210> SEQ ID NO 3
<211> LENGTH: 548
<212> TYPE: DNA
<213> ORGANISM: Homo sapiens
<220> FEATURE:
<221> NAME/KEY: CDS
<222> LOCATION: (23)..(403)
<223> OTHER INFORMATION:

<400> SEQUENCE: 3

```
atagtggaga tggggtcttg ct atg ttt ccc agc agg atg aag ctc tcc act      52
                         Met Phe Pro Ser Arg Met Lys Leu Ser Thr
                         1               5                   10 ggc atc att ttc tgc tcc ctg gtc ctg ggt gtc agc agc caa gga tgg      100
Gly Ile Ile Phe Cys Ser Leu Val Leu Gly Val Ser Ser Gln Gly Trp
            15                  20                  25 tta aca ttc ctc aag gca gct ggc caa ggg gca aaa gac atg tgg aga      148
Leu Thr Phe Leu Lys Ala Ala Gly Gln Gly Ala Lys Asp Met Trp Arg
        30                  35                  40 gcc tac tct gac atg aaa gaa gcc aat tac aaa aaa tca gac aaa tac      196
Ala Tyr Ser Asp Met Lys Glu Ala Asn Tyr Lys Lys Ser Asp Lys Tyr
    45                  50                  55 ttc cat gct cgg ggg aac tat gat gct gta caa agg ggc cct ggg ggt      244
Phe His Ala Arg Gly Asn Tyr Asp Ala Val Gln Arg Gly Pro Gly Gly
60                  65                  70 gtc tgg gct aca gaa gtg atc agc gat gcc aga gag aac gtc cag aga      292
Val Trp Ala Thr Glu Val Ile Ser Asp Ala Arg Glu Asn Val Gln Arg
75                  80                  85                  90 ctc aca gga gac cat gca gag gat tcg ctg gct ggc cag gct acc aac      340
Leu Thr Gly Asp His Ala Glu Asp Ser Leu Ala Gly Gln Ala Thr Asn
                95                  100                 105 aaa tgg ggc cag agt ggc aaa gac ccc aat cac ttc cga cct gct ggc      388
Lys Trp Gly Gln Ser Gly Lys Asp Pro Asn His Phe Arg Pro Ala Gly
            110                 115                 120 ctg cca gag aaa tac tgagcttctt ttcaatctgc tctgaggaga cctgctgtga     443
Leu Pro Glu Lys Tyr
        125 ccctgagggc aggacattt gttgacctac agttacttga attctatatc cctagtactt     503 gatatagaac acataaaaat gcttaataaa tgcttgtgaa atcca                    548
```

<210> SEQ ID NO 4
<211> LENGTH: 127
<212> TYPE: PRT
<213> ORGANISM: Homo sapiens

<400> SEQUENCE: 4

```
Met Phe Pro Ser Arg Met Lys Leu Ser Thr Gly Ile Ile Phe Cys Ser
1               5                   10                  15

Leu Val Leu Gly Val Ser Ser Gln Gly Trp Leu Thr Phe Leu Lys Ala
            20                  25                  30

Ala Gly Gln Gly Ala Lys Asp Met Trp Arg Ala Tyr Ser Asp Met Lys
        35                  40                  45

Glu Ala Asn Tyr Lys Lys Ser Asp Lys Tyr Phe His Ala Arg Gly Asn
    50                  55                  60

Tyr Asp Ala Val Gln Arg Gly Pro Gly Gly Val Trp Ala Thr Glu Val
65                  70                  75                  80

Ile Ser Asp Ala Arg Glu Asn Val Gln Arg Leu Thr Gly Asp His Ala
                85                  90                  95

Glu Asp Ser Leu Ala Gly Gln Ala Thr Asn Lys Trp Gly Gln Ser Gly
            100                 105                 110

Lys Asp Pro Asn His Phe Arg Pro Ala Gly Leu Pro Glu Lys Tyr
        115                 120                 125
```

<210> SEQ ID NO 5
<211> LENGTH: 23
<212> TYPE: DNA

<213> ORGANISM: Homo sapiens

<400> SEQUENCE: 5
gatgaagctc tccactggca tca     23

<210> SEQ ID NO 6
<211> LENGTH: 25
<212> TYPE: DNA
<213> ORGANISM: Homo sapiens

<400> SEQUENCE: 6
tcagagtagg ctctccacat gtctt     25

<210> SEQ ID NO 7
<211> LENGTH: 33
<212> TYPE: DNA
<213> ORGANISM: Homo sapiens

<400> SEQUENCE: 7
aacttgaaac agaatgtgta ttatccttgg ttg     33

<210> SEQ ID NO 8
<211> LENGTH: 26
<212> TYPE: DNA
<213> ORGANISM: Homo sapiens

<400> SEQUENCE: 8
cagctgcctt gaggaatgtt aaccat     26

<210> SEQ ID NO 9
<211> LENGTH: 21
<212> TYPE: DNA
<213> ORGANISM: Homo sapiens

<400> SEQUENCE: 9
gctgctgaca cccaggacca g     21

<210> SEQ ID NO 10
<211> LENGTH: 28
<212> TYPE: DNA
<213> ORGANISM: Homo sapiens

<400> SEQUENCE: 10
agcaggatga agctctcctc tggcatca     28

<210> SEQ ID NO 11
<211> LENGTH: 31
<212> TYPE: DNA
<213> ORGANISM: Homo sapiens

<400> SEQUENCE: 11
cagccaagga tggttaacat tcctcaaggc a     31

<210> SEQ ID NO 12
<211> LENGTH: 6
<212> TYPE: DNA
<213> ORGANISM: Homo sapiens

<400> SEQUENCE: 12 ctggga     6

<210> SEQ ID NO 13
<211> LENGTH: 9

```
<212> TYPE: DNA
<213> ORGANISM: Homo sapiens

<400> SEQUENCE: 13 ttccsggaa                                                                    9

<210> SEQ ID NO 14
<211> LENGTH: 9
<212> TYPE: DNA
<213> ORGANISM: Homo sapiens

<400> SEQUENCE: 14 ttccwggaa                                                                    9

<210> SEQ ID NO 15
<211> LENGTH: 9
<212> TYPE: DNA
<213> ORGANISM: Homo sapiens

<400> SEQUENCE: 15 ttcccggaa                                                                    9

<210> SEQ ID NO 16
<211> LENGTH: 10
<212> TYPE: DNA
<213> ORGANISM: Homo sapiens

<400> SEQUENCE: 16
ttccaaggaa                                                                  10
```